(12) United States Patent
Hamauzu

(10) Patent No.: US 12,042,314 B2
(45) Date of Patent: Jul. 23, 2024

(54) RADIOGRAPHIC IMAGE PROCESSING DEVICE, RADIOGRAPHIC IMAGE PROCESSING METHOD, AND RADIOGRAPHIC IMAGE PROCESSING PROGRAM

(71) Applicant: FUJIFILM Corporation, Tokyo (JP)

(72) Inventor: Shin Hamauzu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 363 days.

(21) Appl. No.: 17/155,442

(22) Filed: Jan. 22, 2021

(65) Prior Publication Data
US 2021/0244370 A1  Aug. 12, 2021

(30) Foreign Application Priority Data
Feb. 7, 2020  (JP) .................................. 2020-019955

(51) Int. Cl.
*A61B 6/12* (2006.01)
*A61B 6/02* (2006.01)
(Continued)

(52) U.S. Cl.
CPC .................. *A61B 6/12* (2013.01); *A61B 6/02* (2013.01); *A61B 6/461* (2013.01);
(Continued)

(58) Field of Classification Search
CPC ........ A61B 17/06066; A61B 17/06166; A61B 17/29; A61B 17/3201; A61B 17/3211; A61B 2017/00115; A61B 2034/2065; A61B 2090/061; A61B 2090/062; A61B 2090/0804; A61B 2090/366;
(Continued)

(56) References Cited

U.S. PATENT DOCUMENTS

2010/0246923 A1* 9/2010 Nathaniel ............ A61B 6/5211
382/286
2016/0206383 A1 7/2016 Leong et al.
(Continued)

FOREIGN PATENT DOCUMENTS

JP  S52-056495 U  4/1977
JP  H09-327452 A  12/1997
(Continued)

OTHER PUBLICATIONS

An Office Action; "Notice of Reasons for Refusal," mailed by the Japanese Patent Office on Dec. 20, 2022, which corresponds to Japanese Patent Application No. 2020-019955 and is related to U.S. Appl. No. 17/155,442; with English language translation.

*Primary Examiner* — Mark D Remaly
(74) *Attorney, Agent, or Firm* — Studebaker & Brackett PC

(57) ABSTRACT

A processor detects a surgical tool from a radiographic image acquired by irradiating a subject with radiation emitted from a radiation source and detecting the radiation transmitted through the subject with a radiation detector. The processor measures a size of the detected surgical tool on the radiographic image. The processor derives a position of the surgical tool in a height direction in the subject on the basis of an actual size of the surgical tool, the measured size, and a geometrical positional relationship between a position of the radiation source and a position of a detection surface of the radiation detector.

18 Claims, 8 Drawing Sheets

(51) Int. Cl.
  *A61B 6/46*    (2024.01)
  *A61B 17/06*   (2006.01)
  *A61B 17/29*   (2006.01)
  *A61B 17/3201*  (2006.01)
  *A61B 17/3211*  (2006.01)
  *A61F 2/07*    (2013.01)
  *A61F 13/44*   (2006.01)
  *G06T 7/62*    (2017.01)
  *G06T 7/70*    (2017.01)

(52) U.S. Cl.
  CPC .. *A61B 17/06066* (2013.01); *A61B 17/06166* (2013.01); *A61B 17/29* (2013.01); *A61B 17/3201* (2013.01); *A61B 17/3211* (2013.01); *A61F 2/07* (2013.01); *A61F 13/44* (2013.01); *G06T 7/62* (2017.01); *G06T 7/70* (2017.01); *G06T 2207/10116* (2013.01); *G06T 2207/30004* (2013.01)

(58) Field of Classification Search
  CPC ..... A61B 2090/376; A61B 34/20; A61B 6/02; A61B 6/12; A61B 6/461; A61B 90/30; A61B 90/37; A61F 13/44; A61F 2/07; G06T 2207/10116; G06T 2207/30004; G06T 7/62; G06T 7/70; G06T 7/73
  See application file for complete search history.

(56) References Cited

U.S. PATENT DOCUMENTS

2016/0302747 A1 10/2016 Averbuch
2018/0279973 A1 10/2018 Schaefer et al.

FOREIGN PATENT DOCUMENTS

| JP | 2011-156321 A | 8/2011 |
| JP | 2016-064118 A | 4/2016 |
| JP | 2016-178986 A | 10/2016 |
| JP | 2016-534832 A | 11/2016 |
| JP | 2017-502807 A | 1/2017 |
| JP | 2018-068863 A | 5/2018 |
| JP | 2018-534969 A | 11/2018 |

\* cited by examiner

RADIOGRAPHIC IMAGE PROCESSING DEVICE, RADIOGRAPHIC IMAGE PROCESSING METHOD, AND RADIOGRAPHIC IMAGE PROCESSING PROGRAM

CROSS REFERENCE TO RELATED APPLICATIONS

The present application claims priority under 35 U.S.C. § 119 to Japanese Patent Application No. 2020-019955 filed on Feb. 7, 2020. The above application is hereby expressly incorporated by reference, in its entirety, into the present application.

BACKGROUND

Technical Field

The present disclosure relates to a radiographic image processing device, a radiographic image processing method, and a radiographic image processing program.

Related Art

Various surgical tools, such as gauze to suppress bleeding, a thread and a suture needle for sewing up a wound or an incision, a scalpel and scissors for incision, a drain for draining blood, and forceps for opening an incision, are used in a case in which a surgical operation is performed for a patient. The surgical tools may cause serious complications in a case in which they remain in the body of the patient after surgery.

Therefore, a method has been proposed which prepares a discriminator that has trained the characteristics of a gauze image, inputs an image acquired by capturing a surgical field with a camera to the discriminator to discriminate whether or not gauze is present, and checks that no surgical tools remain in the body of the patient after surgery (see JP2018-068863A).

However, since gauze is stained with blood, it is difficult to find gauze in the image acquired by the camera even in a case in which the discriminator is used. Further, a small surgical tool, such as a suture needle, is likely to go between the internal organs. Therefore, it is difficult to find the surgical tool in the image acquired by the camera even in a case in which the discriminator is used. In contrast, it is considered that a radiographic image of the patient is acquired after surgery and is observed to check whether or not a surgical tool remains in the body of the patient. However, since both the operator and the nurse are tired after long surgery, the possibility of missing the remaining surgical tools is high.

SUMMARY OF THE INVENTION

The present disclosure has been made in view of the above-mentioned problems and an object of the present disclosure is to provide a technique that can reliably prevent a surgical tool from remaining in the body of a patient after surgery.

According to the present disclosure, there is provided a radiographic image processing device comprises at least one processor. The processor detects a surgical tool from a radiographic image acquired by irradiating a subject with radiation emitted from a radiation source and detecting the radiation transmitted through the subject with a radiation detector, measures a size of the detected surgical tool on the radiographic image, and derives a position of the surgical tool in a height direction in the subject on the basis of an actual size of the surgical tool, the measured size, and a geometrical positional relationship between a position of the radiation source and a position of a detection surface of the radiation detector.

The "height direction" is a direction in which the radiation is transmitted in the subject and is aligned with, for example, the direction of the optical axis of the radiation emitted from the radiation source.

In addition, in the radiographic image processing device according to the present disclosure, the processor may display the radiographic image on a display such that the position of the surgical tool in the height direction is visually recognizable.

Further, the radiographic image processing device according to the present disclosure may further comprise a light source that irradiates a position where the surgical tool is detected in the subject with spot light.

Furthermore, in the radiographic image processing device according to the present disclosure, the processor may change at least one of the size, color, or brightness of the spot light according to the position of the surgical tool in the height direction.

Moreover, in the radiographic image processing device according to the present disclosure, the surgical tool may include at least one of gauze, a scalpel, scissors, a drain, a suture needle, a thread, forceps, or a stent graft.

Further, in the radiographic image processing device according to the present disclosure, at least a portion of the gauze may include a radiation absorbing thread.

According to the present disclosure, there is provided a radiographic image processing method comprising: detecting a surgical tool from a radiographic image acquired by irradiating a subject with radiation emitted from a radiation source and detecting the radiation transmitted through the subject with a radiation detector; measuring a size of the detected surgical tool on the radiographic image; and deriving a position of the surgical tool in a height direction in the subject on the basis of an actual size of the surgical tool, the measured size, and a geometrical positional relationship between a position of the radiation source and a position of a detection surface of the radiation detector.

In addition, a program that causes a computer to perform the radiographic image processing method may be provided.

According to the present disclosure, it is possible to reliably prevent a surgical tool from remaining in the body of a patient after surgery.

DETAILED DESCRIPTION

Figure 1:
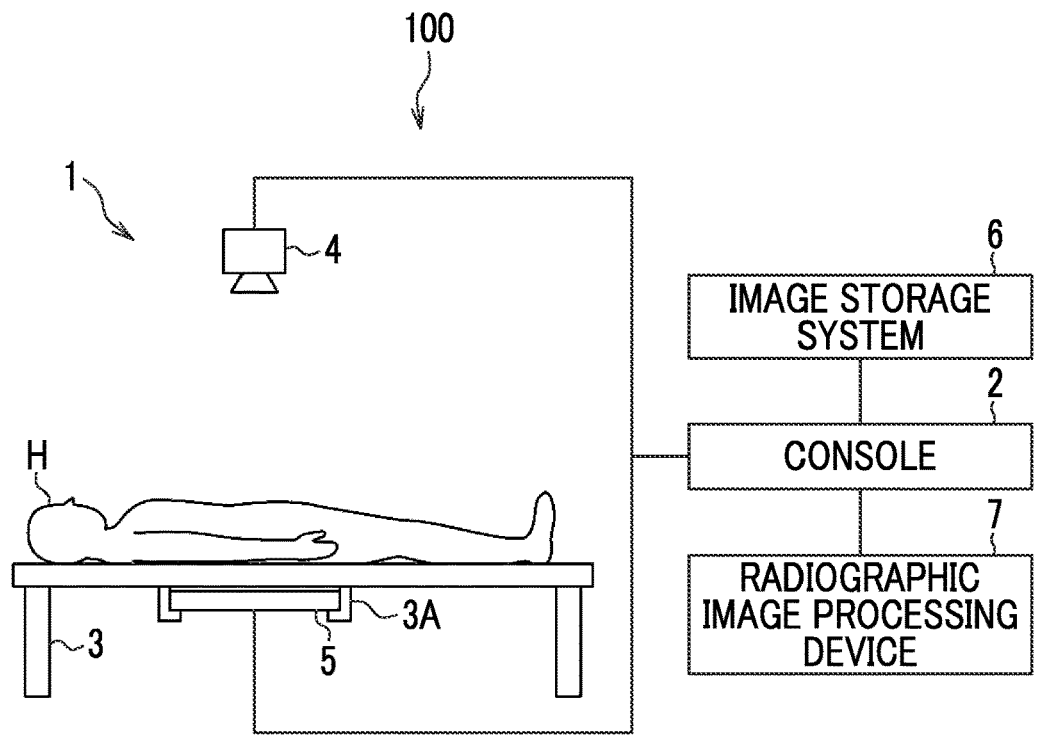
FIG. 1 is a block diagram schematically illustrating a configuration of a radiography system to which a radiographic image processing device according to a first embodiment of the present disclosure is applied.

Hereinafter, embodiments of the present disclosure will be described with reference to the drawings. FIG. 1 is a block diagram schematically illustrating a configuration of a radiography system to which a radiographic image processing device according to a first embodiment of the present disclosure is applied. As illustrated in FIG. 1, a radiography system 100 according to this embodiment acquires a radiographic image of a subject that is a patient after a surgical operation and detects a surgical tool included in the radiographic image. The radiography system 100 according to this embodiment comprises an imaging apparatus 1, a console 2, an image storage system 6, and a radiographic image processing device 7.

The imaging apparatus 1 detects radiation, which has been emitted from a radiation source 4, such as an X-ray source, and transmitted through a subject H, with a radiation detector 5 to acquire a radiographic image G0 of the subject H that lies supine on an operating table 3. The radiographic image G0 is input to the console 2.

The radiation detector 5 is a portable radiation detector and is attached to the operating table 3 by an attachment portion 3A that is provided in the operating table 3. In addition, the radiation detector 5 may be fixed to the operating table 3.

The console 2 has a function of controlling the imaging apparatus 1 using, for example, an imaging order and various kinds of information acquired from a radiology information system (RIS) (not illustrated) or the like through a network, such as a wireless communication local area network (LAN), and commands or the like directly issued by an engineer or the like. For example, in this embodiment, a server computer is used as the console 2.

The image storage system 6 is a system that stores image data of the radiographic images captured by the imaging apparatus 1. The image storage system 6 extracts an image corresponding to a request from, for example, the console 2 and the radiographic image processing device 7 from the stored radiographic images and transmits the image to a device that is the source of the request. A specific example of the image storage system 6 is a picture archiving and communication system (PACS).

Figure 2:
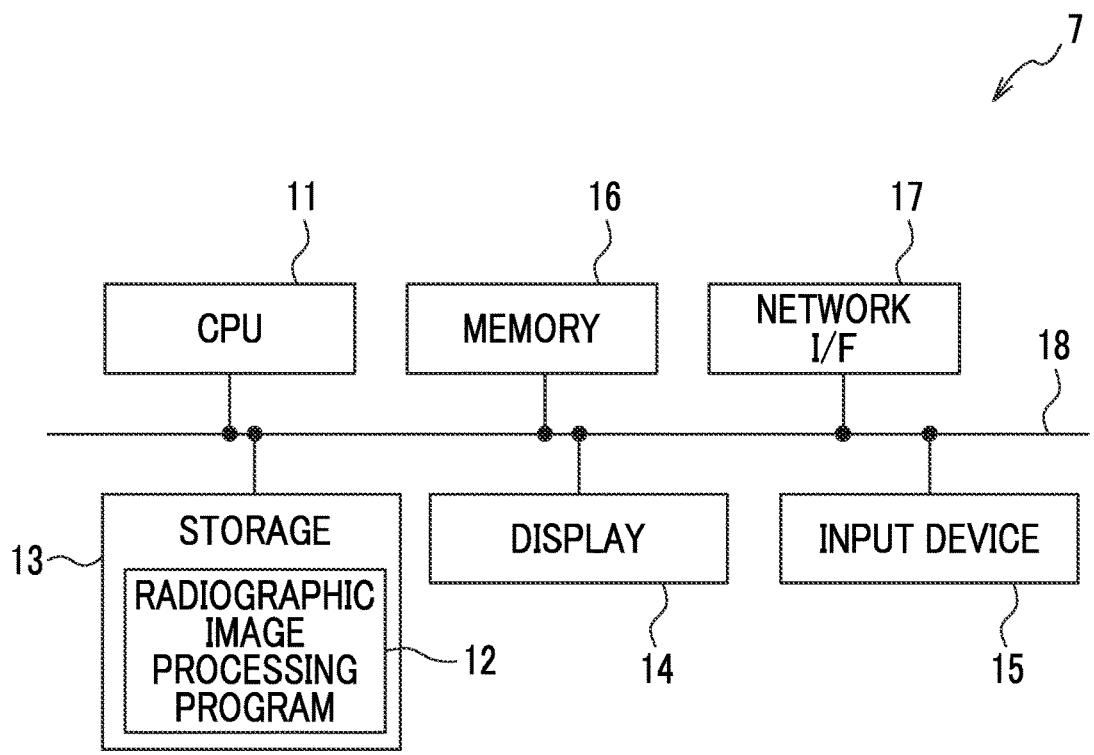
FIG. 2 is a diagram schematically illustrating a configuration of the radiographic image processing device according to the first embodiment.

Next, the radiographic image processing device according to this embodiment will be described. First, the hardware configuration of the radiographic image processing device according to this embodiment will be described with reference to FIG. 2. As illustrated in FIG. 2, the radiographic image processing device 7 is a computer, such as a workstation, a server computer, or a personal computer, and comprises a central processing unit (CPU) 11, a non-volatile storage 13, and a memory 16 as a temporary storage area. In addition, the radiographic image processing device 7 comprises a display 14, such as a liquid crystal display, an input device 15, such as a keyboard and a mouse, and a network interface (I/F) 17 that is connected to a network 10. The CPU 11, the storage 13, the display 14, the input device 15, the memory 16, and the network I/F 17 are connected to a bus 18. The CPU 11 is an example of a processor according to the present disclosure.

The storage 13 is implemented by, for example, a hard disk drive (HDD), a solid state drive (SSD), and a flash memory. A radiographic image processing program 12 installed in the radiographic image processing device 7 is stored in the storage 13 as a storage medium. The CPU 11 reads out the radiographic image processing program 12 from the storage 13, expands it in the memory 16, and executes the expanded radiographic image processing program 12.

In addition, the radiographic image processing program 12 is stored in a storage device of the server computer connected to the network or a network storage so as to be accessed from the outside and is downloaded and installed in the computer forming the radiographic image processing device 7 on demand. Alternatively, the programs are recorded on a recording medium, such as a digital versatile disc (DVD) or a compact disc read only memory (CD-ROM), are distributed and installed in the computer forming the radiographic image processing device 7 from the recording medium.

Figure 3:
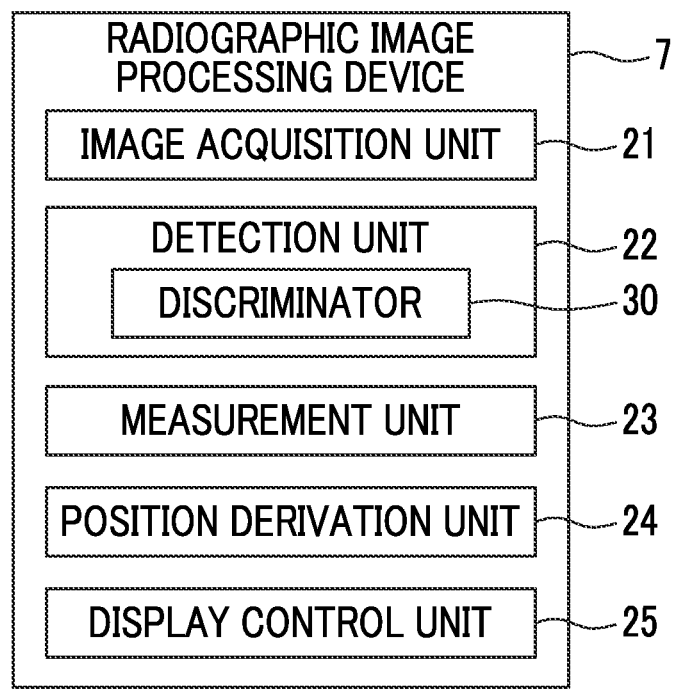
FIG. 3 is a diagram illustrating a functional configuration of the radiographic image processing device according to the first embodiment.

Next, the functional configuration of the radiographic image processing device according to the first embodiment will be described. FIG. 3 is a diagram illustrating the functional configuration of the radiographic image processing device according to the first embodiment. As illustrated in FIG. 3, the radiographic image processing device 7 comprises an image acquisition unit 21, a detection unit 22, a measurement unit 23, a position derivation unit 24, and a display control unit 25. Then, the CPU 11 executes the radiographic image processing program 12 to function as the image acquisition unit 21, the detection unit 22, the measurement unit 23, the position derivation unit 24, and the display control unit 25.

The image acquisition unit 21 drives the radiation source 4 to irradiate the subject H that has undergone surgery with radiation and detects the radiation transmitted through the subject H using the radiation detector 5 to acquire the radiographic image G0. In this case, the image acquisition unit 21 sets imaging conditions, such as the type of target and filter used in the radiation source 4, an imaging dose, a tube voltage, and a source image receptor distance (SID).

The detection unit 22 detects a region of the surgical tool in the radiographic image G0. For the detection, a discriminator 30 that discriminates the region of the surgical tool included in the radiographic image G0 in a case in which the radiographic image G0 is input is applied to the detection unit 22. In a case in which the target radiographic image G0 is input to the detection unit 22, the detection unit 22 directs the discriminator 30 to discriminate the region of the surgical tool included in the radiographic image G0, thereby detecting the region of the surgical tool.

Here, the discriminator 30 is constructed by training a machine learning model using the radiographic image including the surgical tool as training data. Further, in this embodiment, it is assumed that gauze is used as the surgical tool.

Figure 4:
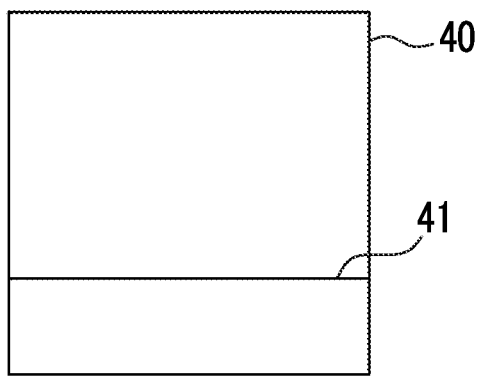
FIG. 4 is a diagram illustrating gauze.
Figure 5:
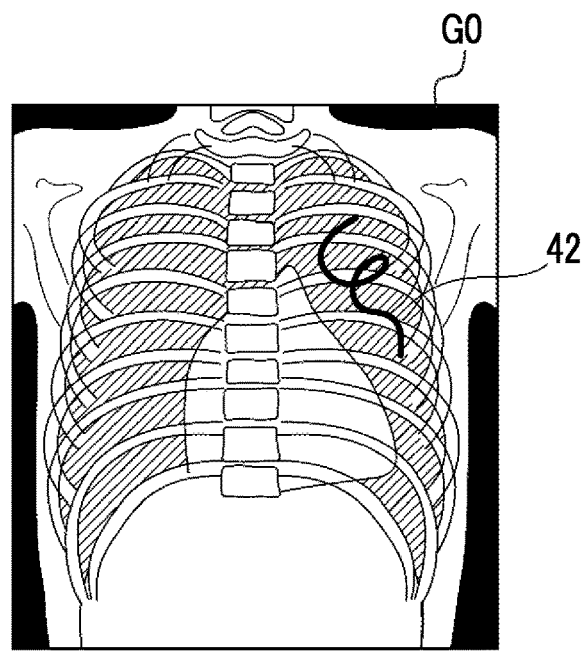
FIG. 5 is a diagram illustrating a radiographic image including a surgical tool.

FIG. 4 is a diagram illustrating gauze. As illustrated in FIG. 4, gauze 40 is a plain-woven cotton fabric and a radiation absorbing thread 41 is woven in a portion of the gauze 40. Cotton yarn transmits radiation and the radiation absorbing thread 41 absorbs radiation. Therefore, the radiographic image of the gauze 40 includes only the linear radiation absorbing thread 41. Here, during surgery, the gauze 40 is rolled and inserted into the human body in order to absorb blood. Therefore, in a case in which the gauze 40 is present in the human body, as illustrated in FIG. 5, a gauze image 42 which is the image of the gauze 40 included in the radiographic image G0 indicates a state in which the radiation absorbing thread 41 is rolled.

The measurement unit 23 measures the size of the surgical tool in the radiographic image G0. That is, the measurement unit 23 measures the length of the gauze image 42 in a case in which the gauze image 42 is detected. The length of the gauze image 42 can be derived by counting the number of pixels warped in the longitudinal direction of the gauze image 42 and multiplying the number of pixels by the pixel size of the radiation detector 5. It is assumed that the length of the gauze image measured by the measurement unit 23 is L1.

The position derivation unit 24 derives the position of the surgical tool in the height direction in the subject H on the basis of the actual size of the surgical tool, the size measured by the measurement unit 23, and the geometrical positional relationship between the position of the radiation source 4 and the position of a detection surface of the radiation detector 5. Specifically, the position derivation unit 24 derives the position of the gauze 40 in the height direction in the subject H on the basis of the actual length L2 of the radiation absorbing thread in the gauze 40, the length L1 of the gauze image 42 measured by the measurement unit 23, and a surface-to-radiation source distance (that is, SID) determined by the position of the radiation source 4 and the position of the detection surface of the radiation detector 5.

Figure 6:
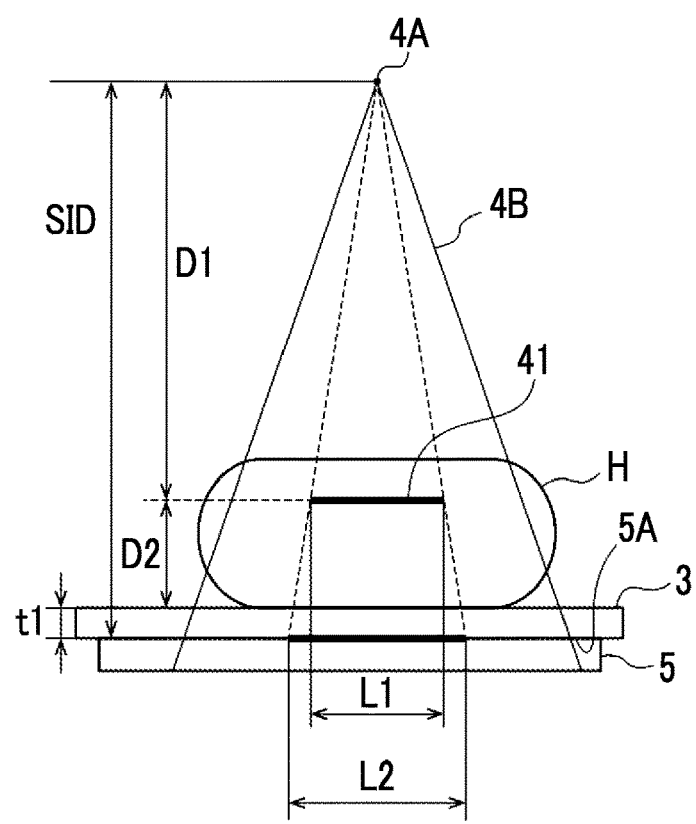
FIG. 6 is a diagram illustrating the measurement of the position of the surgical tool in a height direction.

FIG. 6 is a diagram illustrating the measurement of the position of the surgical tool in the height direction. In addition, in FIG. 6, a radiation absorbing thread 41 included in the gauze 40 which is the surgical tool included in the subject H is represented by a straight line for the purpose of explanation. As illustrated in FIG. 6, radiation 4B emitted from a focus 4A of the radiation source 4 is diffused, and the subject H is irradiated with the radiation 4B. Then, a detection surface 5A of the radiation detector 5 is irradiated with the radiation 4B transmitted through the subject H. As illustrated in FIG. 6, in a case in which the distance from the focus 4A to the detection surface 5A of the radiation detector 5 is SID and the distance from the focus 4A to the radiation absorbing thread 41 of the gauze 40 in the subject H is D1, D1 is represented by the following Expression (1) using SID, L1, and L2.

$$D1 = SID \times L1/L2 \quad (1)$$

In addition, the position derivation unit 24 may use the distance D1 as the position of the surgical tool in the height direction, or may derive a distance D2 from a surface of the operating table 3 to the gauze 40 as the position of the surgical tool in the height direction using the following Expression (2). Further, in Expression (2), t1 is the height of the operating table 3. In this embodiment, it is assumed that the distance D2 is derived as the position of the surgical tool in the height direction.

$$D2 = SID - D1 - t1 \quad (2)$$

Figure 7:
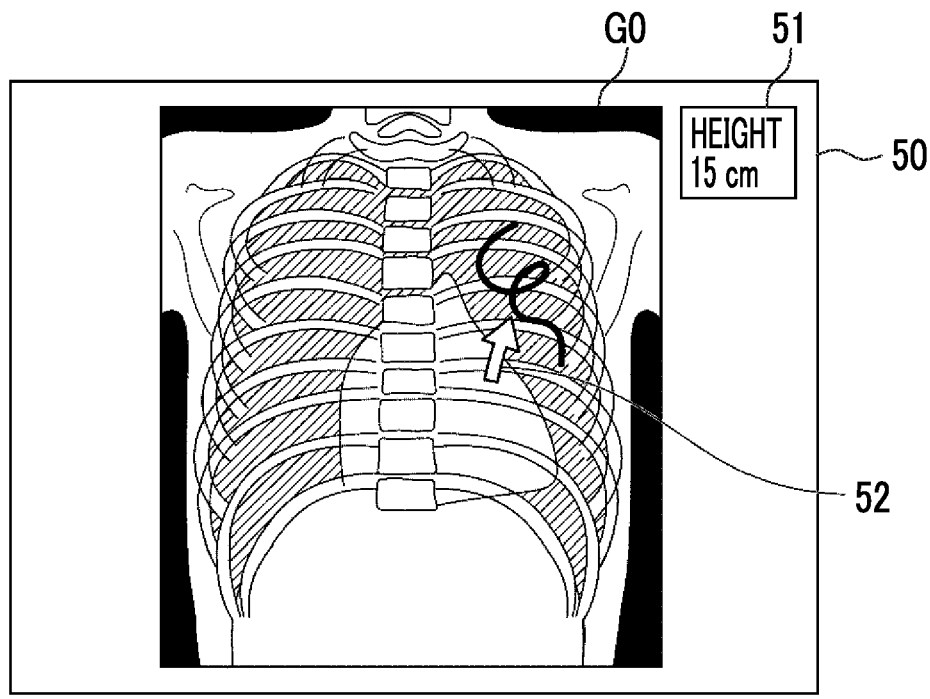
FIG. 7 is a diagram illustrating a radiographic image display screen.

In a case in which the detection unit 22 detects the region of the surgical tool from the radiographic image G0, the display control unit 25 displays the radiographic image G0 on the display 14 such that the position of the surgical tool in the height direction can be visually recognized. FIG. 7 is a diagram illustrating a radiographic image display screen. As illustrated in FIG. 7, the radiographic image G0 and height information 51 indicating the height position of the surgical tool from the surface of the operating table 3 are displayed on a display screen 50. Further, in FIG. 7, the height information 51 indicates that "the height is 15 cm". In the radiographic image G0, an arrow-shaped mark 52 is displayed in the vicinity of the region of the surgical tool included in the radiographic image G0 such that the region of the surgical tool is highlighted. Instead of giving the mark 52, for example, the region of the surgical tool may be surrounded with a frame so as to be highlighted.

Furthermore, in a case in which the radiographic image G0 is displayed on the display 14, image processing for display, such as a gradation conversion process or a density conversion process, may be performed on the radiographic image G0 in order for the user to easily observe the displayed radiographic image G0. The display control unit 25 may perform the image processing for display, or an image processing unit for performing the image processing for display may be separately provided. In addition, in a case in which the image processing for display is performed on the radiographic image G0, the detection unit 22 may detect the region of the surgical tool from the radiographic image G0 subjected to the image processing for display.

Figure 8:
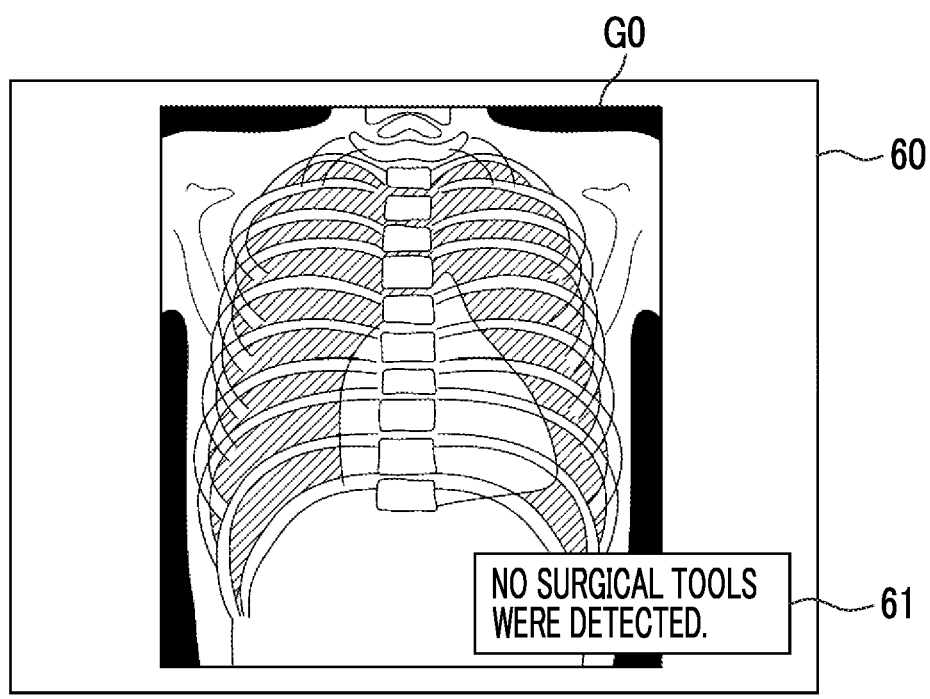
FIG. 8 is a diagram illustrating a notification screen in a case in which a region of the surgical tool is not detected.

Further, in a case in which the detection unit 22 does not detect the region of the surgical tool from the radiographic image G0, the display control unit 25 notifies the fact. FIG. 8 is a diagram illustrating a notification screen in a case in which no surgical tools have been detected. As illustrated in FIG. 8, a message 61 of "No surgical tools were detected." is displayed on a notification screen 60 so as to be superimposed on the radiographic image G0. In addition, instead of the message 61, for example, an icon or a mark indicating that no surgical tools have been detected may be displayed. Further, the turn-on and turn-off of the display of the message 61 may be switched by a command from the input device 15.

Figure 9:
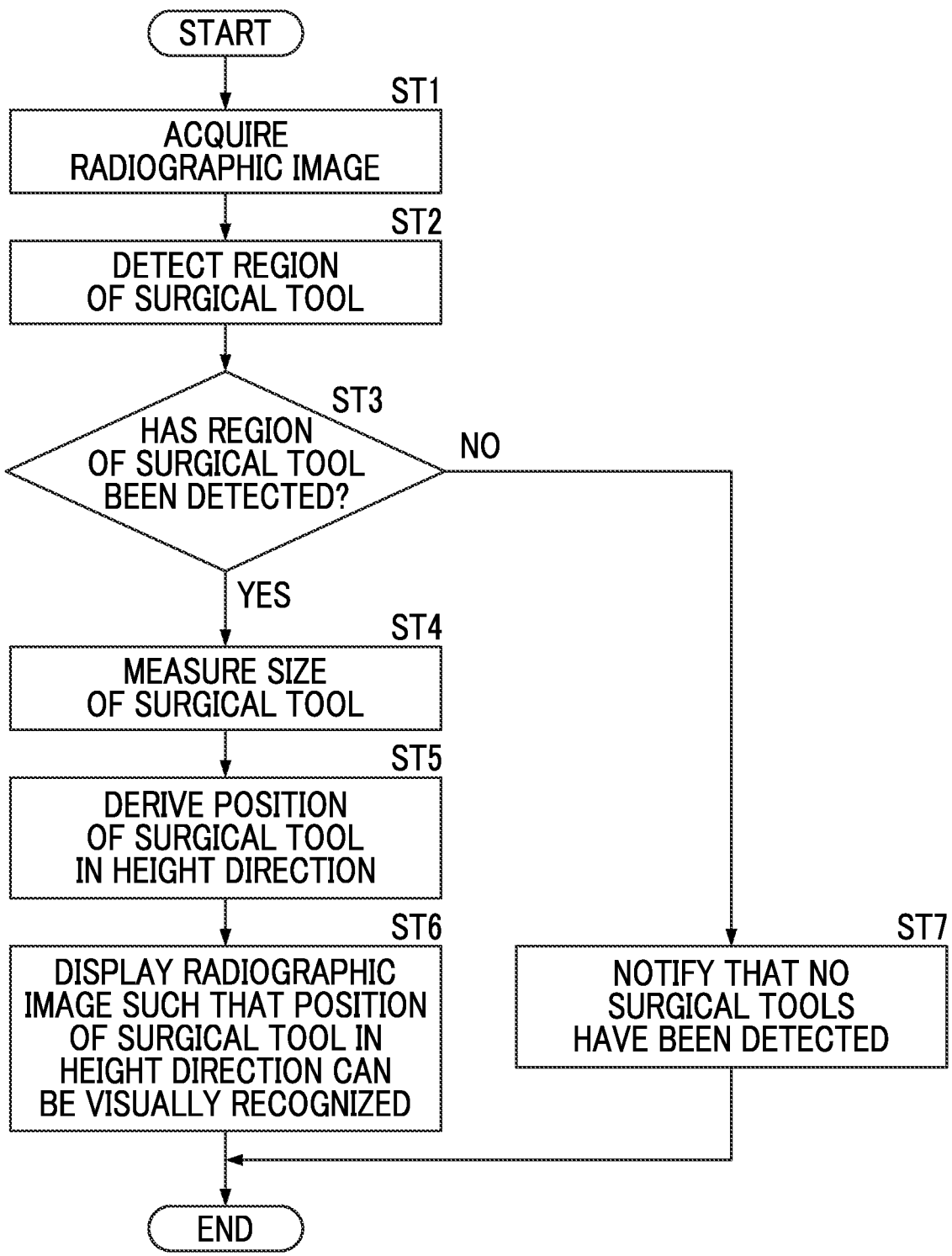
FIG. 9 is a flowchart illustrating a process performed in the first embodiment.

Next, a process performed in the first embodiment will be described. FIG. 9 is a flowchart illustrating a detection process performed in the first embodiment. The image acquisition unit 21 acquires the radiographic image G0 as a detection target (Step ST1), and the detection unit 22 detects the region of the surgical tool from the radiographic image G0 (Step ST2).

In a case in which the region of the surgical tool has been detected from the radiographic image G0 (Step ST3: YES), the measurement unit 23 measures the size of the surgical tool in the radiographic image G0 (Step ST4). Then, the position derivation unit 24 derives the position of the surgical tool in the height direction in the subject H on the basis of the actual size of the surgical tool, the size measured by the measurement unit 23, and the geometrical positional relationship between the position of the radiation source 4 and the position of the detection surface of the radiation detector 5 (Step ST5). Then, the display control unit 25 displays the radiographic image G0 on the display 14 such that the position of the surgical tool in the height direction can be visually recognized (Step ST6). Then, the process ends. On the other hand, in a case in which the region of the surgical tool has not been detected in Step ST3, the display control unit 25 notifies that the region of the surgical tool has not been detected (notification that no surgical tools have been detected; Step ST7). Then, the process ends.

As such, in the first embodiment, in a case in which the surgical tool has been detected from the radiographic image G0, the size of the surgical tool is measured, and the position of the surgical tool in the height direction in the subject H is derived. Therefore, the radiographic image G0 is displayed such that the position of the surgical tool in the height direction can be visually recognized, which makes it possible to check how deep the surgical tool is present from the surface of the subject H. Therefore, even in an exhausted situation after surgery, it is possible to easily search for the surgical tool that is present in the subject H. As a result, it is possible to reliably prevent the surgical tool from remaining in the body of the patient who is the subject H after surgery.

Further, in the first embodiment, in a case in which the region of the surgical tool has not been detected in the radiographic image G0, the fact is notified. Therefore, the operator can recognize that no surgical tools remain in the body of the patient who is the subject H.

Figure 10:
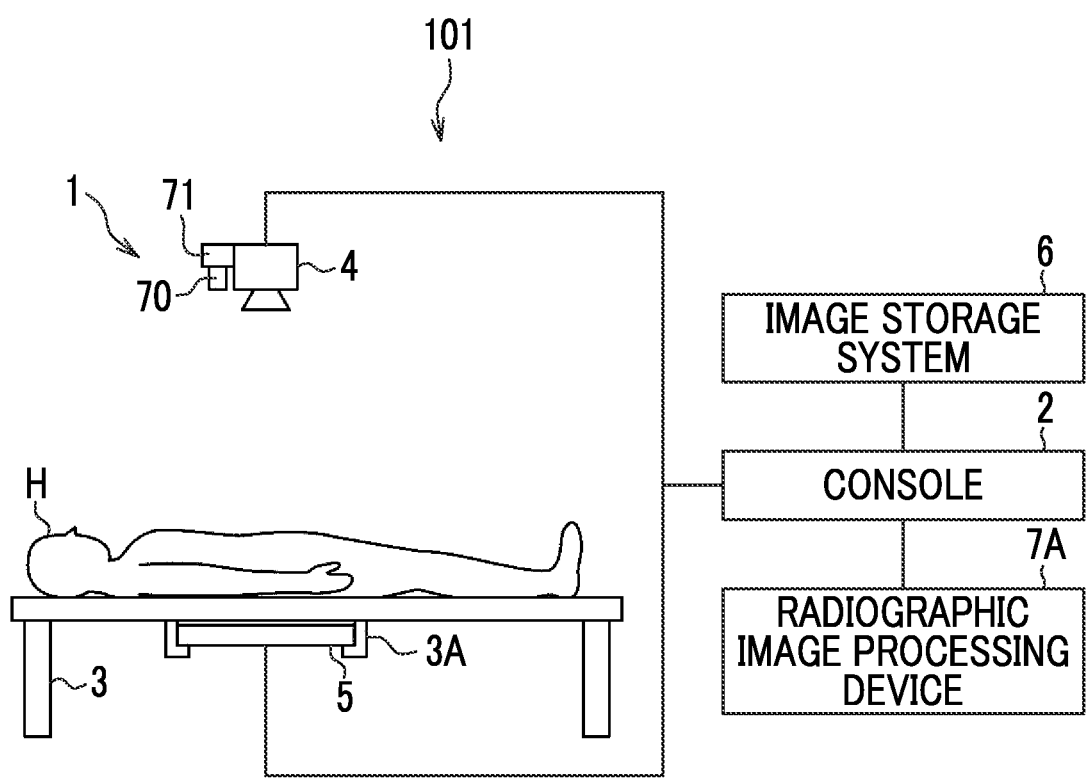
FIG. 10 is a block diagram schematically illustrating a configuration of a radiography system to which a radiographic image processing device according to a second embodiment of the present disclosure is applied.

Next, a second embodiment of the present disclosure will be described. FIG. 10 is a block diagram schematically illustrating a configuration of a radiography system to which a radiographic image processing device according to the second embodiment of the present disclosure is applied. In FIG. 10, the same components as those in FIG. 1 are denoted by the same reference numerals, and the detailed description thereof will not be repeated. The second embodiment is different from the first embodiment in that a radiography system 101, to which the radiographic image processing device according to the second embodiment is applied, comprises a light source 70 that emits spot light to the position where a surgical tool has been detected in the subject H and a light source driving unit 71 that drives the light source 70.

The light source 70 consists of, for example, a light emitting diode (LED) that can change the color of light to be emitted. Further, the light source 70 is provided with a diaphragm (not illustrated) for changing the size of the spot light to be emitted.

The light source driving unit 71 changes the color of the spot light emitted from the light source 70, changes the size of an aperture of the diaphragm, or changes the brightness of the spot light in response to a command from an irradiation control unit which will be described below. In addition, the direction of the light source 70 is changed such that the position where the surgical tool has been detected in the subject H is irradiated with the spot light. Therefore, the light source driving unit 71 is provided with an electric circuit (not illustrated) for changing the color of the spot light or changing the brightness of the spot light and a driving mechanism (not illustrated) for changing the direction of the light source 70 or opening and closing the diaphragm.

In addition, the spatial positional relationship between the light source 70 and the surface of the radiation detector 5 is known. Further, the position of the surgical tool detected in the radiographic image G0 is matched with the position on the surface of the radiation detector 5. Therefore, the light source driving unit 71 changes the direction of the light source 70 such that the position of the surgical tool in the radiation detector 5 is irradiated with the spot light.

Figure 11:
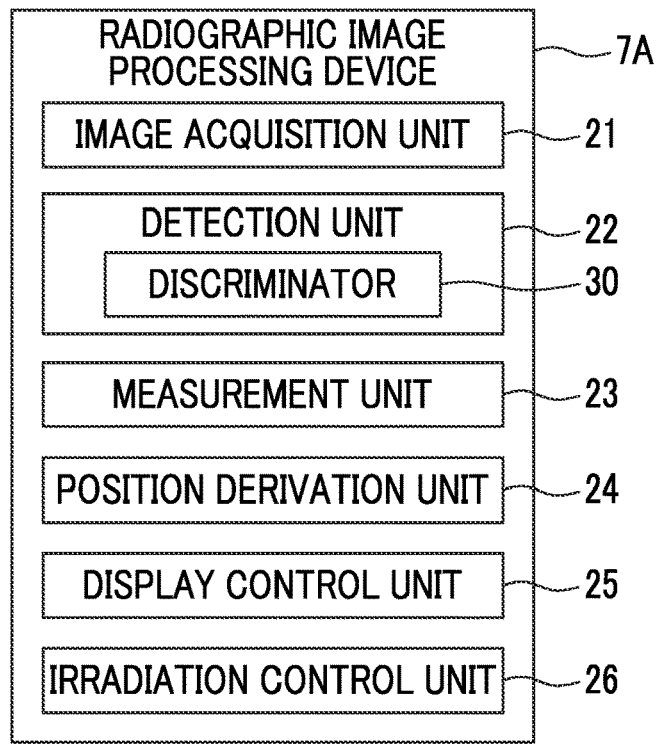
FIG. 11 is a diagram illustrating a functional configuration of the radiographic image processing device according to the second embodiment.

FIG. 11 is a diagram illustrating the functional configuration of the radiographic image processing device according to the second embodiment. Further, in FIG. 11, the same components as those in FIG. 3 are denoted by the same reference numerals, and the detailed description thereof will not be repeated. A radiographic image processing device 7A according to the second embodiment is different from that in the first embodiment in that it comprises an irradiation control unit 26.

The irradiation control unit 26 changes at least one of the size, color, or brightness of the spot light emitted by the light source 70 according to the position of the surgical tool in the height direction derived by the position derivation unit 24. For the change, the irradiation control unit 26 outputs a control signal for controlling the light source 70 to the light source driving unit 71. For example, in a case in which the size of the spot light is changed according to the position of the surgical tool in the height direction, the irradiation control unit 26 outputs a control signal for changing the size of the aperture of the diaphragm included in the light source 70 to the light source driving unit 71 such that the size of the spot light becomes larger as the position of the surgical tool becomes further away from the surface of the operating table 3. In addition, the size of the spot light may become smaller as the position of the surgical tool becomes further away from the surface of the operating table 3.

Further, in a case in which the color of the spot light is changed according to the position of the surgical tool in the height direction, for example, the irradiation control unit 26 outputs a control signal for changing the color of the slot light emitted by the light source 70 to the light source driving unit 71 such that the color of the spot light becomes warmer as the position of the surgical tool becomes further away from the surface of the operating table 3 and becomes colder as the position becomes closer to the surface of the operating table 3. In addition, the color of the spot light may become colder as the position of the surgical tool becomes further away from the surface of the operating table 3 and may become warmer as the position becomes closer to the surface of the operating table 3. Further, the change in the color of the spot light according to the position of the surgical tool in the height direction is not limited thereto.

In a case in which the brightness of the spot light is changed according to the position of the surgical tool in the height direction, a control signal for making the spot light brighter as the position of the surgical tool becomes further away from the surface of the operating table 3 is output to the light source driving unit 71. In addition, the spot light may become darker as the position of the surgical tool becomes further away from the surface of the operating table 3.

Figure 12:
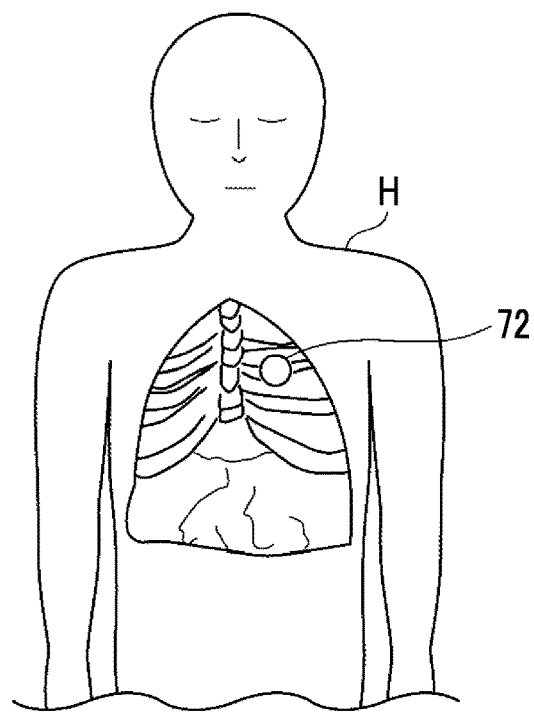
FIG. 12 is a diagram illustrating the irradiation of a subject with spot light.

FIG. 12 is a diagram illustrating the subject H irradiated with the spot light. In a case in which the surgical tool has been detected from the radiographic image G0, the subject H is irradiated with spot light 72 having a size corresponding to the position of the surgical tool in the height direction.

Figure 13:
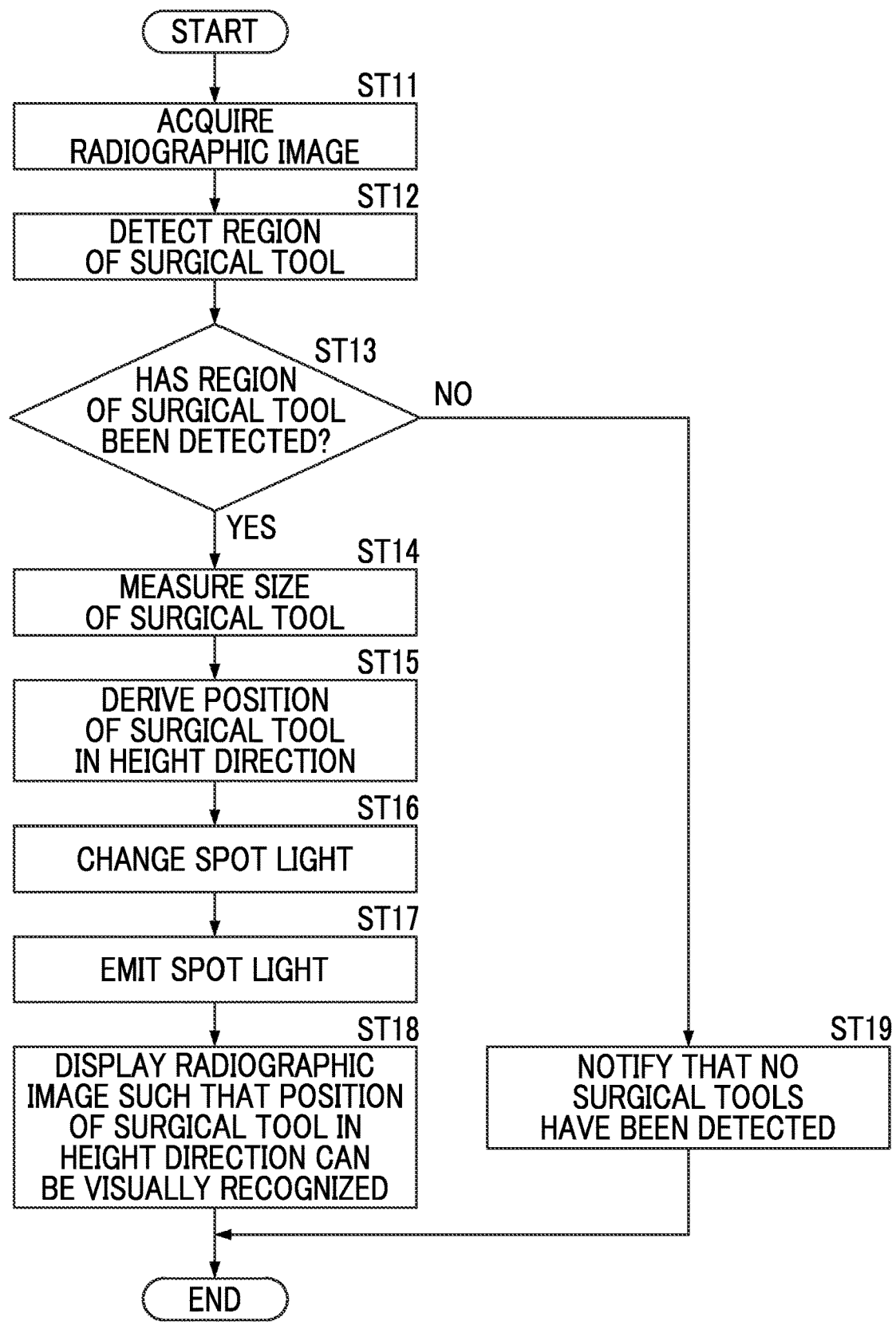
FIG. 13 is a flowchart illustrating a process performed in the second embodiment.

Next, a process performed in the second embodiment will be described. FIG. 13 is a flowchart illustrating a detection process performed in the second embodiment. The image acquisition unit 21 acquires the radiographic image G0 as a detection target (Step ST11), and the detection unit 22 detects the region of the surgical tool from the radiographic image G0 (Step ST12).

In a case in which the region of the surgical tool has been detected from the radiographic image G0 (Step ST13: YES), the measurement unit 23 measures the size of the surgical tool in the radiographic image G0 (Step ST14). Then, the position derivation unit 24 derives the position of the surgical tool in the height direction in the subject H on the basis of the actual size of the surgical tool, the size measured by the measurement unit 23, and the geometrical positional relationship between the position of the radiation source 4 and the position of the detection surface of the radiation detector 5 (Step ST15).

Then, the irradiation control unit 26 outputs, to the light source driving unit 71, a control signal for changing at least one of the size, color, or brightness of the spot light emitted from the light source 70 according to the position of the surgical tool in the height direction (spot light change: Step ST16). The light source driving unit 71 changes at least one of the size, color, or brightness of the spot light emitted from the light source 70 in response to the control signal such that the spot light is emitted from the light source 70 and the position where the surgical tool is detected in the subject H is irradiated with the spot light (Step ST17). Further, the display control unit 25 displays the radiographic image G0 on the display 14 such that the position of the surgical tool in the height direction can be visually recognized (Step ST18). Then, the process ends.

On the other hand, in a case in which the region of the surgical tool has not been detected in Step ST13, the display control unit 25 notifies that the region of the surgical tool has not been detected (notification that no surgical tools have been detected; Step ST19). Then, the process ends.

As such, in the second embodiment, in a case in which the surgical tool has been detected from the radiographic image G0, at least one of the size, color, or brightness of the spot light emitted by the light source 70 is changed according to the position of the surgical tool in the height direction, and the position of the surgical tool in the subject H is irradiated with the spot light. Therefore, it is possible to check at which position of the subject H the surgical tool is present and how deep the surgical tool is present from the surface of the subject H. Therefore, even in an exhausted situation after surgery, it is possible to easily search for the surgical tool that is present in the subject H. As a result, it is possible to reliably prevent the surgical tool from remaining in the body of the patient after surgery.

In addition, in the second Embodiment, the radiographic image G0 is displayed on the display 14 such that the position of the surgical tool in the height direction can be visually recognized. However, the present disclosure is not limited thereto. Only the irradiation with the spot light may be performed without displaying the radiographic image G0 on the display 14.

Further, in each of the above-described embodiments, the suture needle as a surgical tool is a detection target. However, the present disclosure is not limited thereto. Any surgical tool used in surgery, such as gauze, a scalpel, scissors, a drain, a thread, forceps, or a stent graft, can be used as the detection target. In this case, the discriminator 30 may be trained so as to discriminate the target surgical tool. In addition, the discriminator 30 may be constructed such that it is trained to detect a plurality of channels and discriminates not only one kind of surgical tool but also a plurality of kinds of surgical tools.

In addition, in each of the above-described embodiments, the radiation is not particularly limited. For example, a-rays or y-rays other than X-rays can be applied.

In the above-described embodiments, for example, the following various processors can be used as a hardware structure of processing units performing various processes, such as the image acquisition unit 21, the detection unit 22, the measurement unit 23, the position derivation unit 24, the display control unit 25, and the irradiation control unit 26. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as the hardware structure.

Furthermore, specifically, an electric circuit (circuitry) obtained by combining circuit elements, such as semiconductor elements, can be used as the hardware structure of the various processors.

What is claimed is:

1. A radiographic image processing device, comprising:
   at least one processor,
   wherein the processor acquires a radiographic image by irradiating a subject with radiation emitted from a radiation source and detecting the radiation transmitted through the subject with a radiation detector;
   detects a surgical tool from the radiographic image;
   in a case in which the surgical tool is detected, acquires a geometrical positional relationship between a position of the radiation source and a position of a detection surface of the radiation detector, a pixel size of the radiation detector, and an actual size of the surgical tool;
   calculates a size of the detected surgical tool on the radiographic image by counting a number of pixels in the radiographic image corresponding to the size of the surgical tool, and multiplying the number of pixels by the pixel size of the radiation detector; and
   derives a distance between the detection surface of the radiation detector and the surgical tool in a height direction, with the height direction being the same as a direction that is perpendicular to the detection surface of the radiation detector, by using the actual size of the surgical tool, the calculated size of the surgical tool, and the geometrical positional relationship between the position of the radiation source and the position of the detection surface of the radiation detector.

2. The radiographic image processing device according to claim 1, further comprising:
   a light source that irradiates a position where the surgical tool is detected in the subject with spot light.

3. The radiographic image processing device according to claim 2,
   wherein the processor changes at least one of the size, color, or brightness of the spot light according to the position of the surgical tool in the height direction.

4. The radiographic image processing device according to claim 1,
wherein the surgical tool includes at least one of gauze, a scalpel, scissors, a drain, a suture needle, a thread, forceps, or a stent graft.

5. The radiographic image processing device according to claim 4,
wherein at least a portion of the gauze includes a radiation absorbing thread.

6. The radiographic image processing device according to claim 1,
wherein the geometrical positional relationship between the position of the radiation source and the position of a detection surface of the radiation detector is an SID (Source Image receptor Distance), and
wherein the processor calculates the distance between the detection surface of the radiation detector and the surgical tool using the equation $H=SID-SID \times L1/L2$, where H is the distance between the detection surface of the radiation detector and the surgical tool, L1 is the calculated size of the surgical tool, and L2 is the actual size of the surgical tool.

7. The radiographic image processing device according to claim 6, further comprising a display,
wherein the processor displays the radiographic image on the display such that the position of the surgical tool in the height direction (H) is visually recognizable.

8. The radiographic image processing device according to claim 1,
wherein the geometrical positional relationship between the position of the radiation source and the position of the detection surface of the radiation detector is an SID (Source Image receptor Distance), and
wherein the processor calculates the distance between the detection surface of the radiation detector and the surgical tool using the equation $H=SID-SID \times L1/L2-t1$, where H is the distance between the detection surface of the radiation detector and the surgical tool, L1 is the calculated size of the surgical tool, L2 is the actual size of the surgical tool, and t1 is the height of an operating table.

9. The radiographic image processing device according to claim 8, further comprising a display,
wherein the processor displays the radiographic image on the display such that the position of the surgical tool in the height direction (H) is visually recognizable.

10. A radiographic imaging system, comprising:
a radiation source irradiating a subject with radiation;
a radiation detector detecting the radiation transmitted through the subject;
a display; and
at least one processor, wherein the processor:
acquires a radiographic image by irradiating a subject with radiation emitted from a radiation source and detecting the radiation transmitted through the subject with a radiation detector;
detects a surgical tool from the radiographic image;
in a case in which the surgical tool is detected, acquires a geometrical positional relationship between a position of the radiation source and a position of a detection surface of the radiation detector, a pixel size of the radiation detector, and an actual size of the surgical tool;
calculates a size of the detected surgical tool on the radiographic image by counting a number of pixels in the radiographic image corresponding to the size of the surgical tool, and multiplying the number of pixels by the pixel size of the radiation detector; and
derives a distance between the detection surface of the radiation detector and the surgical tool in a height direction of the detection surface of the radiation detector by using the actual size of the surgical tool, the calculated size of the surgical tool, and the geometrical positional relationship between the position of the radiation source and the position of the detection surface of the radiation detector.

11. The radiographic imaging system according to claim 10,
wherein the geometrical positional relationship between the position of the radiation source and the position of a detection surface of the radiation detector is an SID (Source Image receptor Distance), and
wherein the processor calculates the distance between the detection surface of the radiation detector and the surgical tool using the equation $H=SID-SID \times L1/L2$, where H is the distance between the detection surface of the radiation detector and the surgical tool, L1 is the calculated size of the surgical tool, and L2 is the actual size of the surgical tool.

12. The radiographic imaging system according to claim 11,
wherein the processor displays the radiographic image on the display such that the position of the surgical tool in the height direction (H) is visually recognizable.

13. The radiographic imaging system according to claim 10,
wherein the geometrical positional relationship between the position of the radiation source and the position of a detection surface of the radiation detector is an SID (Source Image receptor Distance), and
wherein the processor calculates the distance between the detection surface of the radiation detector and the surgical tool using the equation $H=SID-SID \times L1/L2-t1$, where H is the distance between the detection surface of the radiation detector and the surgical tool, L1 is the calculated size of the surgical tool, L2 is the actual size of the surgical tool, and t1 is the height of an operating table.

14. The radiographic imaging system according to claim 13,
wherein the processor displays the radiographic image on the display such that the position of the surgical tool in the height direction (H) is visually recognizable.

15. The radiographic imaging system according to claim 10, further comprising:
a light source that irradiates a position where the surgical tool is detected in the subject with spot light.

16. The radiographic imaging system according to claim 15,
wherein the processor changes at least one of the size, color, or brightness of the spot light according to the position of the surgical tool in the height direction.

17. The radiographic imaging system according to claim 10,
wherein the surgical tool includes at least one of gauze, a scalpel, scissors, a drain, a suture needle, a thread, forceps, or a stent graft.

18. The radiographic imaging system according to claim 17,
wherein at least a portion of the gauze includes a radiation absorbing thread.

* * * * *